United States Patent [19]
Weiberth

[11] Patent Number: 5,747,708
[45] Date of Patent: May 5, 1998

[54] RETRACTABLE BATCH REACTOR SAMPLER

[75] Inventor: Franz Josef Weiberth, Belle Mead, N.J.

[73] Assignee: Hoechst Marion Roussel, Inc., Cincinnati, Ohio

[21] Appl. No.: 745,765

[22] Filed: Nov. 8, 1996

Related U.S. Application Data

[63] Continuation-in-part of Ser. No. 384,999, Feb. 7, 1995, abandoned.

[51] Int. Cl.⁶ .................................................. G01N 1/12
[52] U.S. Cl. ................................................. 73/863.81
[58] Field of Search ........................ 73/863.31, 863.81, 73/863.82, 863.85, 863.86, 864.31, 864.34, 864.35, 864.51, 864.73, 864.74, 864.64

[56] References Cited

U.S. PATENT DOCUMENTS

| | | | |
|---|---|---|---|
| 2,516,097 | 7/1950 | Woodham et al. | 73/864.64 |
| 3,091,969 | 6/1963 | Romanchuk et al. | 73/863.31 |
| 3,162,049 | 12/1964 | Blanchard | 73/863.85 |
| 4,442,721 | 4/1984 | Singer | 73/863.31 |
| 4,669,321 | 6/1987 | Meyer | 73/863.85 |
| 5,134,879 | 8/1992 | Wong et al. | 73/863.85 |
| 5,341,692 | 8/1994 | Sher et al. | 73/864.51 |

FOREIGN PATENT DOCUMENTS 185004  11/1906  Germany ................ 73/863.81

*Primary Examiner*—Robert Raevis
*Attorney, Agent, or Firm*—Ruth E. Homan

[57] ABSTRACT

This application relates to a retractable batch reactor sampler that is temporarily attached to a reactor, for use in sampling small volumes of a reaction mixture within a reactor on single or multiple occasions, and then detached from the reactor, all without affecting an inert gas blanket already existing within the reactor.

2 Claims, 4 Drawing Sheets

RETRACTABLE BATCH REACTOR SAMPLER

"This is a continuation-in-part of application Ser. No. 08/384,999, filed Feb. 7, 1995, now abandoned".

This application relates to a retractable batch reactor sampler that is temporarily attached to a reactor, for use in sampling small volumes of a reaction mixture within the reactor on single or multiple occasions and then detached from the reactor, all without affecting an inert gas blanket already existing within the reactor, and to the use of the retractable batch reactor sampler.

Several devices for direct sampling of batch reactors are known and many are commercially available. However, these devices suffer from deficiencies which make them unsuitable, inefficient, or unsafe to use in a pilot plant and/or with batch reactors in general.

One type of batch sampler is an immersion device that withdraws samples through the top of a reactor using a vacuum source or a self-priming pump. Some disadvantages of this type of sampler include lines that can clog during the process of taking a sample, fugitive emissions which are generated and a "dead volume" that necessitates a back-venting and rinsing of some lines to the sample device to prevent cross-contamination of samples.

Another example of a batch reactor is an in-line pipe sampler. These samplers typically have a recycle loop comprised of a pump and a series of isolation valves to continuously circulate the reactor contents in a piping loop, usually from the bottom of the reactor to the top. The sample is withdrawn from a device somewhere in the piping loop. These sampling systems generally are bulky and complicated and, for small reactor systems, can contain a significant proportion of the reaction volume in the loop. Furthermore, the presence of valves and pump increases the possibility of chemical leaks and fugitive emissions, and, in the worst case of a serious valve or pump seal failure, the loss of a batch and/or a chemical spill. Additionally, if the reaction volume is a slurry, the lines and valves can clog, thus rendering the sampler inoperable.

Another known type of batch reactor sampling system involves sampling through sample ports that are situated below the liquid level of the reactor by opening valves, or by inserting a syringe needle through a septum or nozzle, often at the sides or near the bottom of the reactor. In these types of systems, the sampling ports can clog when solids settle, and "dead volumes" necessitate rinsing of lines by withdrawing large sample volumes to the sample device to minimize cross-contamination of samples. In addition, a leak or failure of a valve or a mistake during sampling could result in a spill and loss of part or all of the batch.

A variation of this type of sampler is described by Thomas, U.S. Pat. No. 3,298,236, where the use of a syringe to sample a reaction mixture is rather straightforward, since the nature of sub-surface sampling is that the sampling port or nozzle is always flooded with reaction mixture. However, there remains a need for a device that withdraws samples from above the reaction mixture and aligns a small sample of the reaction mixture with the means of removing a sample, such as a syringe needle.

Yet another example of a batch reactor sampler requires opening of the reactor manhole or nozzle and direct immersion of a sampler. Sample is then removed directly, or first through a chamber. While this procedure is simple, it risks exposing to air not only the sample, but the whole reaction mixture also, as well as possible operator exposure to vapors, fugitive emissions and fire (static spark) hazard.

A variation of this type of sampler is described by Blanchard, U.S. Pat. No. 3,162,049, where sample is removed by submerging a bulky sample cup which is fastened to the end of a rod, pulling the cup into a large chamber, then opening the chamber to the atmosphere in order to remove the sample. Thus, there remains a need for a compact device suitable for large and small reactor systems that can be used to withdraw a single sample or multiple samples, either simultaneously or consecutively, under an inert atmosphere without exposing the sample or samples, or the reaction mixture, to air or a non-controlled atmosphere at any time, and without generating waste or fugitive emissions.

Thus, it is an object of this invention to provide for a sampling device that allows the sampling to take place in an inert atmosphere.

It is also an object of this invention to provide for a sampling device that allows multiple samples to be withdrawn, simultaneously or consecutively, in an inert atmosphere.

It is also an object of this invention to provide for a compact sampling device which can be used on relatively small reactors.

It is also an object of this invention to provide for withdrawing small sample volumes.

It is also an object of this invention to provide a sampling device which has little "dead volume" and is relatively easy to decontaminate after each sample is taken.

It is also an object of this invention to provide a sampling device with which varying sample volumes can be withdrawn.

It is also an object of this invention to provide a sampling device from which no waste or fugitive emissions are generated during sampling operations.

These and other objects are accomplished in accordance with the invention by providing a device and method for efficiently removing samples from a batch reactor. The device comprises a sampler element and a sampler chamber unit comprising an attachment element, a sampling element and an atmosphere control element. The sampler element passes by sliding through the sampler chamber unit.

More particularly, the device comprises a sampler element such as a sampling rod with one or more sample cavities on one end which provides the means for a sample to be obtained from the reaction mixture; and a sampler chamber unit comprising an attachment element which provides the means for attaching the sampler chamber to the reaction vessel, such as a threaded nipple attached to an isolation valve that is mounted onto a flange on the reaction vessel or a quick-connect coupler attached to a nozzle on the reactor or reaction vessel; a sampling element which is also an alignment element and is the means for placing a sample in the proper position for removal from the sampler unit and the means for removing the sample; a gland element which is the means for supporting the sampling rod while allowing it to slide through the sampler chamber; and an atmosphere control element which is the means for controlling the content of the atmosphere within the reaction vessel such as by infusing an inert gas into the reactor.

In operation, the sampler chamber unit with the sampling rod in the fully-retracted position is attached to an isolation valve on the reactor and optionally the interior of the sampler chamber unit is purged with an inert gas. The isolation valve on the reactor is then opened and the sampling rod is slid through the sampler chamber unit, the isolation valve, and the reactor until the sample cavity is submerged in the reaction mixture and fills with sample. The sampling rod is then slid in the reverse direction until the sample cavity is retracted into the sample chamber unit so that the sample cavity is aligned with the alignment element. Only the precise portion of the sample in the sample cavity that is needed for analysis is then removed through the alignment element using a syringe. The portion of the sample remaining in the sample cavity is then returned to the reaction mixture for flushing and/or additional sampling. In this way, consecutive sampling operations can be performed without subjecting the sample or the reactor's contents to air or an uncontrolled atmosphere at any time before, during, in-between or after the sampling process; a precise amount of sample can be withdrawn and any unused sample can be returned without generating waste or fugitive emissions; and operators do not come in contact with the sample or the reactor's contents. Alternatively, the isolation valve can be closed, and the sampling rod can be removed for cleaning and/or replacement.

For a better understanding of the invention as well as other features and objects thereof, reference is made to the following detailed description taken in conjunction with the accompanying drawings wherein.

Figure 1:
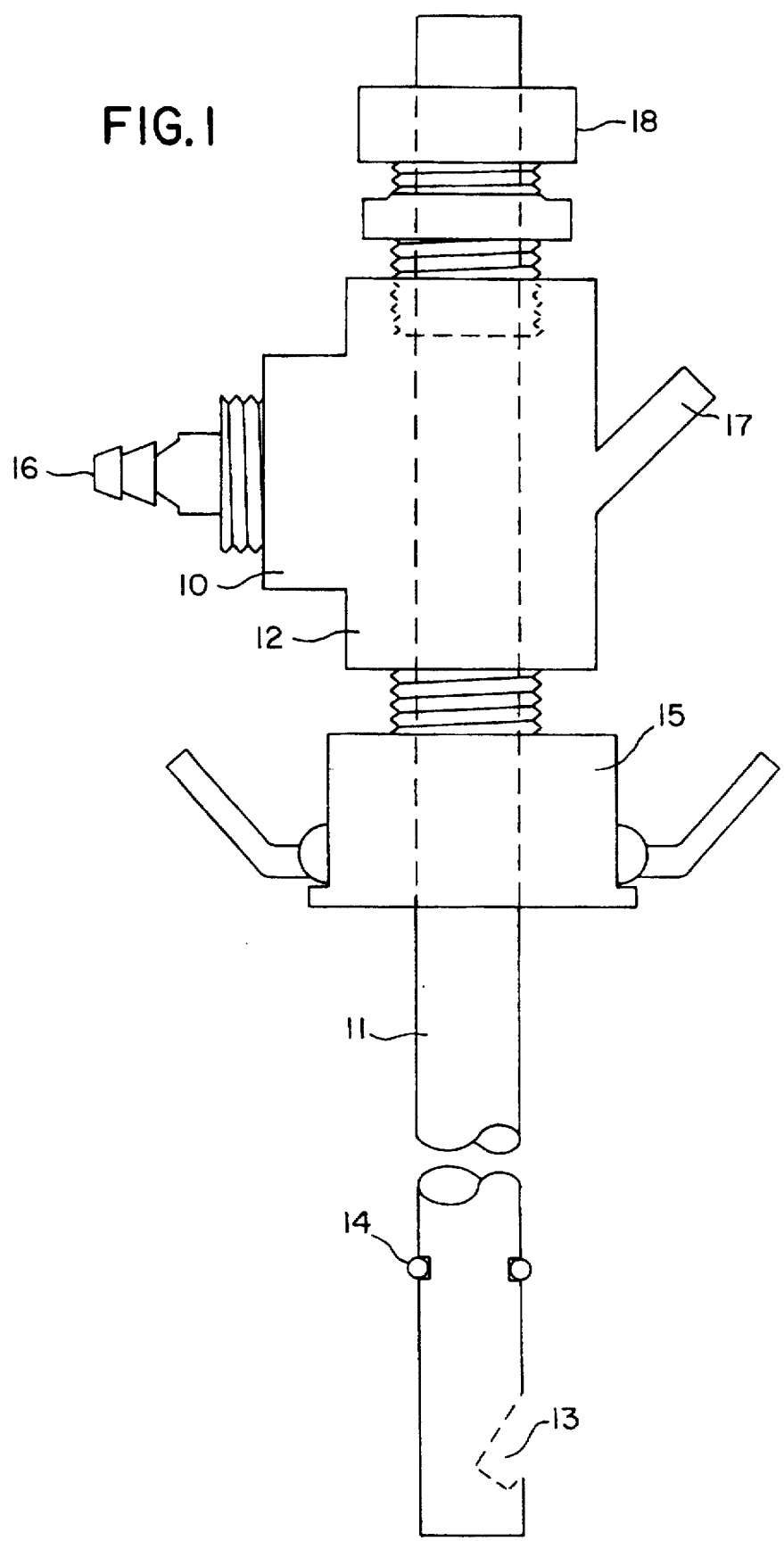
FIG. 1 is a schematic view of one embodiment of a sampler device according to the invention.

Referring to FIG. 1 there is seen a preferred embodiment of a batch reactor sampler 10 according to the invention. The sampler 10 comprises a sampler element 11 and a sampler chamber unit 12.

The sampler element 11 in this embodiment is a rod which slides up and down within the sampler chamber unit. The rod is long enough to extend from the bottom of the reaction vessel to the top of the sampler chamber unit. A sample cavity 13 is located at the end of the sampler element 11 that can be slid into the reaction vessel. A stop 14 is on the sampler element 11 between the sample cavity 13 and the other end of the sampler element and positions the sample cavity 13 in line with tube 17.

In the case of a support chamber 12 completely or partially constructed of glass, the sample cavity 13 is visually positioned.

Turning now to the sampler chamber unit 12, it can be seen that it comprises a means 15 for attaching the sampler chamber unit to the reaction vessel; a means 16 for infusing into the sampler chamber unit an inert gas so as to maintain an inert atmosphere, a means 17 to remove the contents of the sample cavity and a means 18 to control the sliding motion of the sampler unit.

In a preferred embodiment of FIG. 1 the means 15 for attaching the sampler support unit to the reaction vessel is a quick-connect coupler attached to a nozzle on the reactor or reaction vessel. Alternatively, if the reactor does not have an isolation valve, a valve can be attached to the sampling device via a modular quick-connect valve assembly as is known in the art. The interior dimension of the valve must be large enough so that the sampler element can pass through.

The means 16 for infusing an inert gas is typically a nipple such as a barbed hose connector or a compression fitting such as those which are known in the art.

The means 17 for removing the contents of the sample cavity 13 is preferably a tube or pipe welded, threaded or fused to the side of the support unit at an angle, preferably about a 45 degree angle. The end is typically fitted with a septum (not shown) such as is known in the art.

The means 18 for allowing the sampler element to slide is typically a threaded adapter having an internal O-ring which allows the sampler element to slide but provides an air-tight seal.

Figure 2:
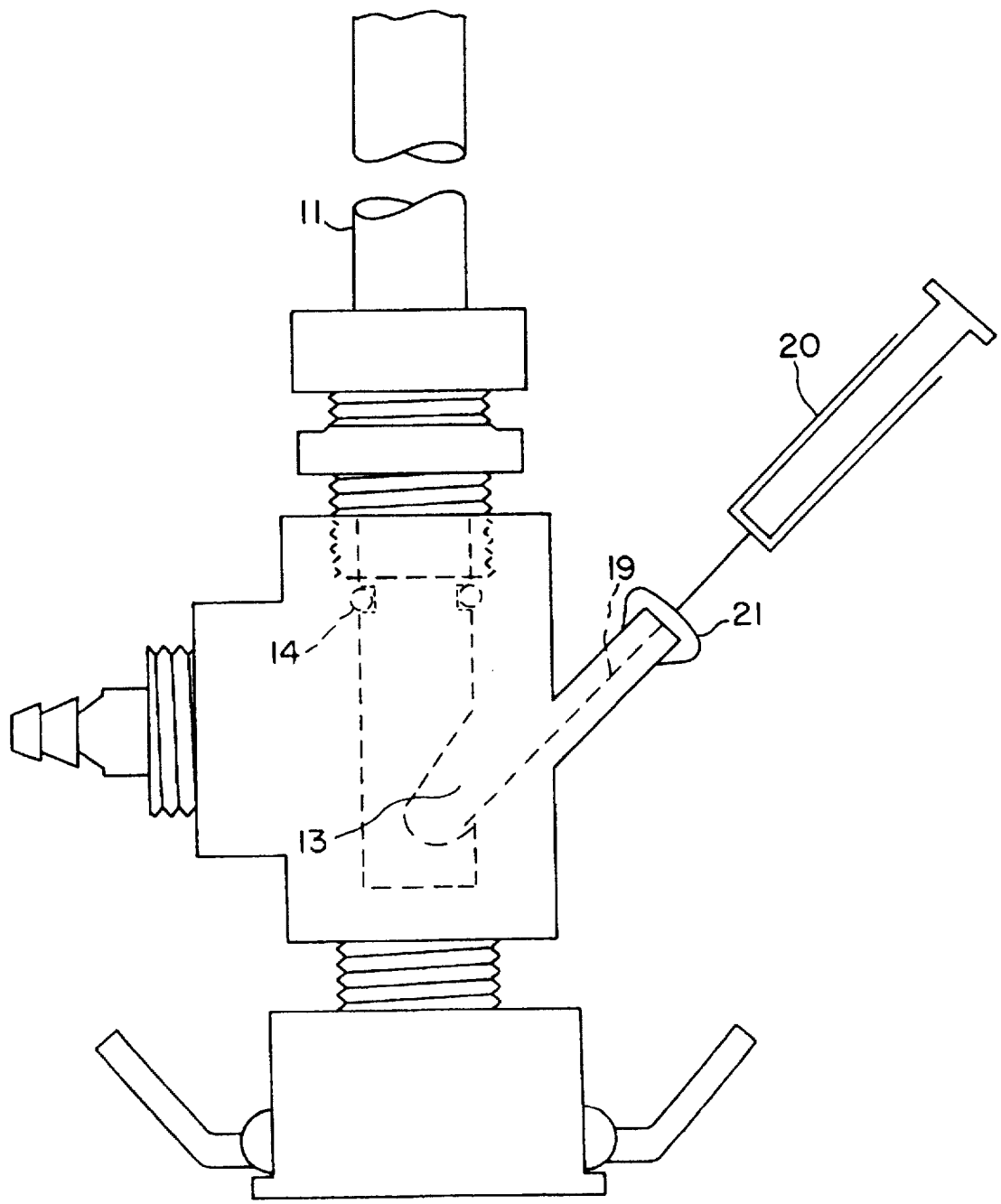
FIG. 2 is a schematic view of one embodiment of the sampling device according to this invention where the sampler chamber unit is constructed of glass, and the sampling rod has multiple sample cavities.

Referring now to FIG. 2, there is seen a view of the embodiment of the invention where the sampler rod 11 is pulled up to the position where the sample is taken. The needle 19 of syringe 20 is inserted through a septum 21 into the sample cavity 13.

Figure 3:
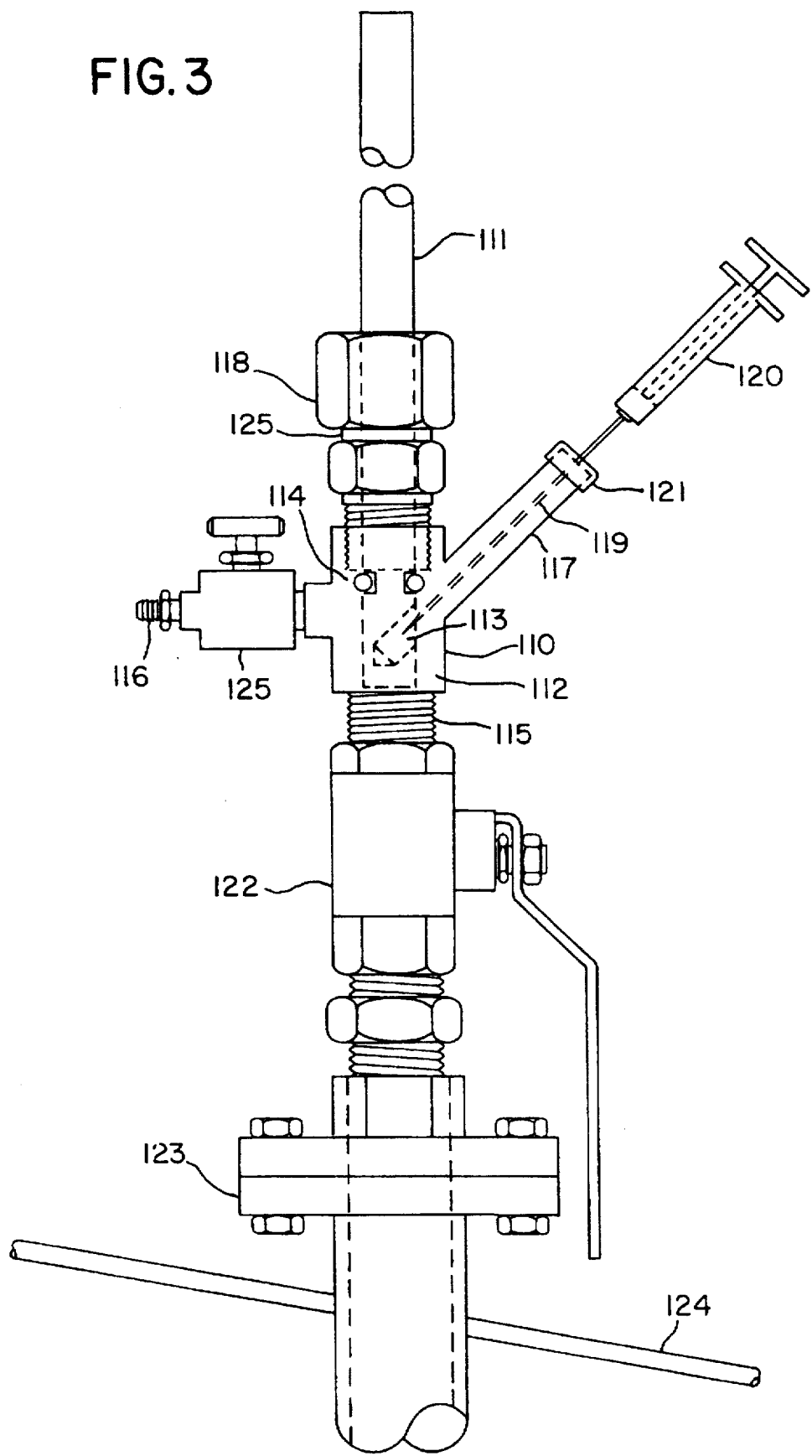
FIG. 3 is a schematic view of a preferred embodiment of the sampler device according to the invention wherein the sampler chamber unit is attached to the reactor by means of a threaded nipple attached to an isolation valve.

Referring to FIG. 3 there is seen a preferred embodiment of a batch reactor sampler 110 according to the invention. The sampler 110 comprises a sampling rod 111 and a sampler chamber unit 112.

The sampling rod 111 in this embodiment is a rod which slides up and down within the sampler chamber unit 112. The sampling rod 111 is long enough to extend from the bottom of reactor 124 to the top of the sampler chamber unit 112. Sample cavity 113 is located at the end of the sampling rod 111 and can be submerged in the reaction mixture as sampling rod 111 is slid into the reactor 124. Sample cavity 113 is bored directly into the sampling rod 111 at about a 45 degree angle in relation to the length of the rod. The configuration of the cavity can be varied to suit sampling requirements since the volume of the cavity, thus the volume of the sample of the reaction mixture, is dependent on the angle, shape and depth of the cavity. A cavity of radius 0.25 inches bored 0.5 inches deep will have a volume of 0.6 milliliters. Thus, sample cavity 113 is an integral part of the sampling rod and no bulky connecting hardware and sampling cups are required. The complete length of sampling rod 111 and sample cavity 113 is thus of uniform diameter, preferably ½–¾ inches, although other sizes can also be used. This one-piece construction and narrowness contributes to compactness necessary for suitability with small reactor systems.

A stop 114 is on the sampling rod 111 and positions the sample cavity 113 in line with alignment element 117.

Turning now to the sampler chamber unit 112, it can be seen that it comprises a means 115 for attaching the sampler chamber unit to the reaction vessel; a means 116 for infusing into the sampler chamber unit an inert gas so as to maintain an inert atmosphere, a means 117 to remove the contents of the sample cavity, and a means 118 to control the sliding motion of the sampling rod.

In the preferred embodiment of FIG. 3 the means 115 for attaching the sampler chamber unit 112 to the reactor 124 is a threaded nipple attached to isolation valve 122 that is mounted onto flange 123. Alternatively, if the reactor does not have an isolation valve, sampler chamber unit 112 can be attached directly to flange 123 via a threaded nipple or quick-connect coupling as is known in the art.

The means 116 for infusing an inert gas is typically a nipple such as a barbed hose connector or a compression fitting such as those which are known in the art and an atmosphere control valve 125 with which the flow of inert gas can be controlled.

The means 117 for removing the contents of the sample cavity 113 is an alignment element, preferably a tube or pipe welded, threaded or fused into the side of the sampler chamber unit 112 at an angle, preferably about a 45 degree angle, or the same bore angle of sample cavity 113. The end is typically fitted with a septum 121 such as is known in the art.

Still referring to FIG. 3, there is seen a view of the embodiment of the invention where the sampling rod 111 is pulled up to the position where the sample is taken. The needle 119 of syringe 120 is inserted through septum 121 and into the sample cavity 113 and removes all or a portion of the sample.

The means 118 for allowing the sampling rod 111 to slide is typically a gland element having an internal seal 126 which allows the sampling rod 111 to slide but provides an air-tight seal.

The interior dimensions of gland element 118, sampler chamber unit 112, attachment element 115, isolation valve 122 and flange 123 must be large enough so that the sampling rod 111 can pass through.

Figure 4:
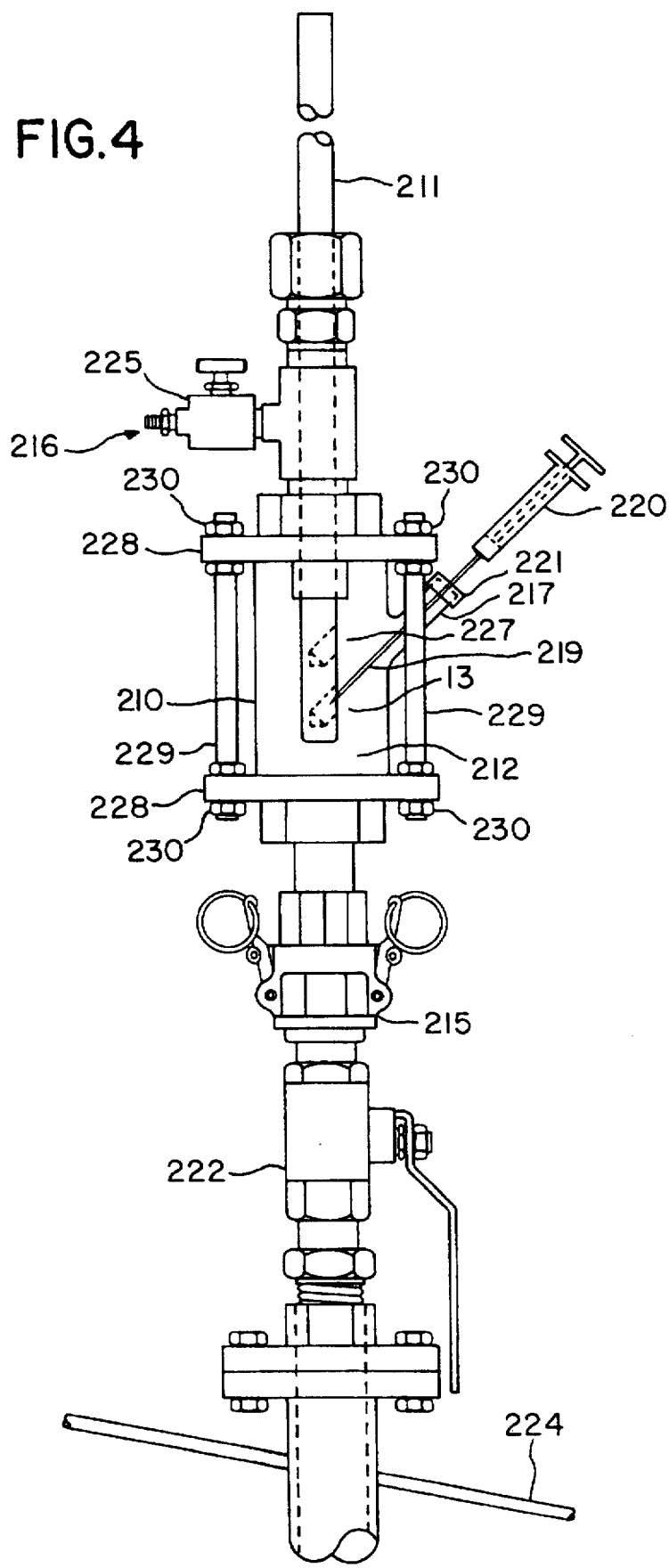
FIG. 4 is a schematic view of a preferred embodiment of the sampler device according to the invention wherein the sampler chamber unit is attached to the reactor by means of a quick-connect coupling.

Referring now to FIG. 4, there is seen another preferred embodiment where the sampler 210 is attached to isolation valve 222 of reactor 224 by way of quick-connect coupling 215. It can be seen that sampler 210 comprises a means to visually align a sample cavity with a syringe needle and withdraw a sample; and a means to take multiple samples of a reaction mixture simultaneously.

The means to visually align a sample cavity with a syringe needle and withdraw a sample is preferably a sampling chamber unit 212 wholly or partially constructed of borosilicate glass or another transparent of translucent material, that is typically held in place between threaded flanges 228 using threaded through-rods 229 and bolt nuts 230 as is known in the art. Sample cavity 213 is visually positioned to align with alignment element 217 that is preferably a glass tube that is fused into the side of sampler chamber unit 212. Needle 219 of syringe 220 is inserted through septum 221 and through alignment element 217 into sample cavity 213 and is used to withdraw all or a precise portion of the sample.

The means to take multiple samples of a reaction mixture simultaneously is a rod with two sample cavities, 213 and 227. Sample cavities 213 and 227 are bored directly into sampling rod 211 and are thus an integral part of the rod. A rod with additional cavities can also be used as required by the sampling needs of the process. The depth and angle of bore of each cavity determines the volume of the cavity. Cavities do not necessarily have to be of identical volume.

The process to use sampler 210 comprises sliding sampling rod 211 into reactor 224 until sample cavities 213 and 227 are submerged; simultaneously filling the cavities with reaction mixture; sliding sampling rod 211 in the reverse direction until sample cavity 227 is retracted into sampler chamber unit 212 and is aligned with alignment element 217; piercing needle 219 through septum 221 and into sample cavity 227; and withdrawing the sample into syringe 220. The process to obtain the sample from the second sample cavity 213 is withdrawing syringe needle 219; sliding sampling rod 211 until sample cavity 213 is aligned with alignment element 217; piercing needle 219 through septum 221 and into sample cavity 213; aid withdrawing the sample into syringe 220.

The process for withdrawing a sample, or withdrawing consecutive samples, under an inert gas blanket atmosphere comprises connecting sampler 210 to closed isolation valve 222 via attachment element 215 while sampling rod 211 in the up (retracted) position; removing septum 221 or positioning it so that it is loosely attached; flushing sampler chamber unit 212 with an inert gas supply provided at connector 216 and by opening atmosphere control valve 225; securing septum 221 to alignment element 217 and closing atmosphere control valve 225; opening isolation valve 222; pushing sampling rod 211 down so that sample cavity 213 is submerged in the reaction mixture; pulling up sampling rod 211 until sample cavity 213 is aligned with alignment element 217; closing isolation valve 222; withdrawing the sample using needle 219 of inert gas purged syringe 220 inserted through septum 221 and into sample cavity 213. At this point, the internals of sampler chamber unit 212 are still under a controlled inert atmosphere, so that the process for subsequent and continued sampling under an inert atmosphere is opening isolation valve 222; pushing sampling rod 211 down so that sample cavity 213 is submerged in the reaction mixture and is flushed and filled with fresh sample; pulling up sampling rod 211 until sample cavity 213 is aligned with alignment element 217; closing isolation valve 222; withdrawing the sample using needle 219 of inert gas purged syringe 220 inserted through septum 221 and into sample cavity 213.

The sample size is generally from about 0.1 mL to about 10 mL, preferably from about 0.2 mL to about 5 mL, depending on the type of analysis which the sample must undergo as is known in the art, and can be varied by utilizing sample rods with varying cavity volumes or varying sizes of syringes.

The sampler is made from materials known in the art such as glass, metals and alloys including stainless steel, or hard plastics including Teflon which are generally non-reactive with the reaction medium. Seals, such as glands and o-rings are made from resilient materials known in the art such as Kalrez® and Viton. The sampling rod is made preferably from polytetrafluoroethylene (PTFE) or materials such as Teflon, carbon-filled Teflon, or other resilient materials. Connections in modifying or preparing the sampler can be made by way of threads, cam locks, quick-connect couplings, flanges, compression fittings or other methods as are known in the art.

While only certain preferred features of the invention have been shown by way of illustration, many modifications and changes will occur to those skilled in the art. It is, therefore, to be understood to cover all such modifications and changes as falling within the true spirit of the invention.

What is claimed is:

1. A retractable batch reactor sampler which comprises a sampling rod and a sampler chamber unit in which the sampler chamber unit is at least partially constructed of a transparent or translucent material, and wherein the sampler chamber has at a first end a means for attaching the sampler chamber unit to a reactor and has at a second end a gland element which supports the sampling rod while allowing the rod to slide through the sampler chamber unit wherein the gland element has an internal seal which allows the sampling rod to slide but provides and air tight seal, between the ends of the sampler chamber unit are positioned a means for controlling the content of the atmosphere within the batch reactor sampler unit, and an alignment element wherein the alignment element is a translucent or transparent tube or pipe which is fixed, to the side of the sampler chamber at about a 45 deg. angle with a first end opening into the sample chamber unit and the second end fitted with a septum; and wherein the sampling rod has a first end extending through the gland element and a second end which passes into the sampler chamber, between the ends of the sampler rod are a multiplicity of sample cavities which are bored into the sampling rod for receiving samples from the reactor, and wherein the complete length of the rod including the cavities is of uniform diameter.

2. A process for simultaneously obtaining multiple representative samples of a reaction mixture in at inert atmosphere using the retractable batch reactor samples of claim 1, which comprises connecting the sampler chamber unit to an isolation valve attached to the reaction vessel wherein the isolation valve is closed with the portion of the sampling rod containing the sample cavities positioned in the sampler chamber unit; flushing the sampler chamber unit with an inert gas while a septum is removed or loosely attached to the alignment element; securing the septum to the end of the alignment element; opening the isolation valve and pushing the sampler element so that the sample cavities are submerged in the reaction mixture and sample is obtained in each sample cavity; pulling the sampling rod until the cavities are contained within the sampler chamber unit, closing the isolation valve; sequentially aligning each of the sample cavities visually with the alignment element; and withdrawing each sample or a portion of each sample using an inert gas purged syringe inserted through the septum and into each of the sample cavities.

* * * * *